United States Patent [19]

Pistorius

[11] 4,160,109

[45] Jul. 3, 1979

[54] CYCLOHEXENE-(1)-DIONE-(3,6)-TETRAALKYLDIKETALS AND PROCESS

[75] Inventor: Rudolf Pistorius, Ober-Mörlen, Fed. Rep. of Germany

[73] Assignee: Hoechst Aktiengesellschaft, Frankfurt am Main, Fed. Rep. of Germany

[21] Appl. No.: 872,450

[22] Filed: Jan. 26, 1978

[30] Foreign Application Priority Data

Jan. 28, 1977 [DE] Fed. Rep. of Germany ....... 2703453

[51] Int. Cl.$^2$ ....................... C07C 41/00; C07C 43/00
[52] U.S. Cl. .................................... 568/667; 260/464; 260/586 R; 568/670; 568/648
[58] Field of Search .................... 260/611 R; 568/670, 568/667

[56] References Cited

U.S. PATENT DOCUMENTS

| 3,127,450 | 3/1964 | Lorette et al. | 260/611 R |
| 3,170,958 | 2/1965 | Howard | 260/611 R |
| 4,082,809 | 4/1978 | Pistorius et al. | 260/611 R |

OTHER PUBLICATIONS

Howard et al., Jour. of Org. Chem., vol. 26 (1961), pp. 1026–1028.

Primary Examiner—Bernard Helfin
Attorney, Agent, or Firm—Curtis, Morris & Safford

[57] ABSTRACT

Cyclohexene-(1)-dione-(3,6)-tetraalkyldiketals of the formula

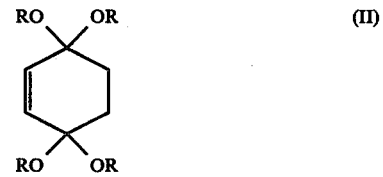

wherein each R is a primary or secondary $C_{1-4}$ alkyl radical are obtained by catalytic hydrogenation of p-benzoquinone tetramethyl-diketal with about 1 mol of $H_2$ per mole of diketal, in a basic medium, at a temperature of from about $-10°$ to $+150°$ C. and optionally by reketalization with a primary or secondary $C_{2-4}$ alcohol in a slightly acid medium with substantial exclusion of water, at a temperature of from about $-10°$ to $+35°$ C. Cyclohexene-(1)-dione-(3,6)-tetraalkyldiketals, optionally dissolved in an alcohol ROH give hydroquinone dialkyl ethers on acidification and heating to about 60° to 120° C., which ethers are valuable dyestuff intermediates. On catalytic hydrogenation in a basic medium, cyclohexene-(1)-dione-(3,6)-tetraalkyldiketals give the corresponding cyclohexane-(1,4)-tetraalkyldiketals, which are the starting products for the manufacture, for example, of tetracyanoquinodimethane, an important compound in the field of semiconductors.

9 Claims, No Drawings

CYCLOHEXENE-(1)-DIONE-(3,6)-TETRAALKYL-DIKETALS AND PROCESS

A p-benzoquinone tetramethyl diketal of the formula

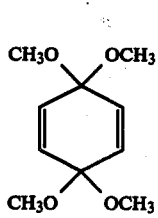

may be prepared, for example by anodic oxidation of anisol or of hydroquinone dimethyl ether in methanol/KOH according to N. L. Weinberg and B. Belleau, Tetrahedron 29 (1973), pages 279 to 285. The compound (I) may be prepared especially suitably by anodic oxidation of benzene, likewise in methanolic solution, this process, however, requiring special conductive salts (cf. British Pat. No. 836,949).

The catalytic reduction of (I) with hydrogen in neutral to slightly acidic medium with stoichiometric consumption of hydrogen gives hydroquinone dimethyl ether in good yield (cf. German Offenlegungsschrift No. 25 47 464), which is a desired intermediate for the preparation of dyestuffs. It is quite natural that the catalytic reduction of (I) to hydroquinone dimethyl ether in neutral to slightly acidic medium is advisable only when anisol or, in particular, benzene is used as the starting compound. Said catalytic reduction, however, involves some difficulties, since frequently an undesired decomposition of (I) occurs. When further investigating the reaction possiblities of (I), in particular during the catalytic hydrogenation, it has been found surprisingly that catalytic hydrogenation in a basic medium results in a product which is completely different from that obtained in hydrogenation in a neutral to slightly acidic medium, namely cyclohexene-(1)-dione-(3,6)-tetramethyldiketal of the formula

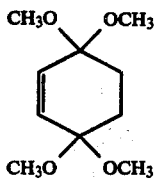

when hydrogenating until about 1 mol of $H_2$ per mol of diketal of the formula I has been absorbed.

It has moreover been found that the diketal of the formula (II) is capable of reketalizing to form the corresponding cyclohexene-(1)-dione-(3,6)-tetraalkyl diketal, when it is dissolved in a higher alkanol than methanol, with substantial exclusion of water, at a temperature approching room temperature and at a slightly acidic pH, and that this diketal, as well as tetramethyl diketal, forms the corresponding hydroquinone dialkyl ether by intramolecular rearrangement while 2 mols of alkanol are split off, when the temperature is increased.

The present invention, consequently, provides first cyclohexene-(1)-dione-(3,6)-tetraalkyl diketals of the formula

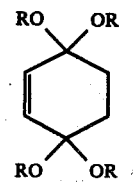

wherein R is a straight chain or branched non-tertiary alkyl radical having of from 1 to 4 carbon atoms, a diketal of the formula (II') with R being $CH_3$, namely cyclohexene-(1)-dione-(3,6)-tetramethyl diketal, being preferred.

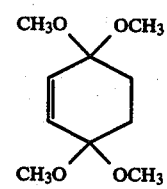

The cyclohexene-(1)-dione-(3,6)-tetraalkyl diketals are prepared in accordance with the invention by reducing p-benzoquinone tetramethyl diketal of the formula (I)

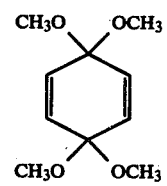

with about 1 mol, more precisely with of from 0.8 to 1.1 mols, preferably of from 0.9 to 1.1 mols and in particular of from 0.95 to 1.0 mol, of $H_2$ per mol of diketal (I) in the presence of a hydrogenation catalyst, in a basic medium, at a temperature of from about $-10°$ to $+150°$ C., preferably of from about $+10°$ to $+50°$ C., in particular of from about $+15°$ to $+40°$ C., and by reketalizing the cyclohexene-(1)-dione-(3,6)-tetramethyl diketal optionally by treating it with an alcohol possessing a $C_{2-4}$ primary or secondary alkyl radical, at a temperature of from about $-10°$ to $35°$ C., preferably of from about $0°$ to $25°$ C. and in particular of from about $+5°$ to $25°$ C., in a slightly acid medium with substantial exclusion of water, to yield a compound of the formula II' with R not being $CH_3$.

The reduction is suitably carried out in a solvent of usual purity which is conventional for use in catalytic hydrogenations, for example acetic acid methyl or -ethyl ester, dioxane, tetrahydrofurane and others. A preferred solvent is methanol or the alcohol ROH, the definition of R corresponding to that for the desired radical R in the final product (II'). The solutions employed for reducing generally contain of from about 10 to 80% by weight, preferably of from about 20 to 50% by weight, of the compound (I).

Preferred catalysts are the noble metal catalysts belonging to group VIII of the periodic table which are conventional for use for catalytic hydrogenations, as such, as well as in the form of their oxides, with or without a carrier material, for example active carbon. Preferred catalysts are palladium and platinum. A suitable catalyst which does not belong to said group is in particular Raney-nickel. The catalysts are employed in usual amounts, preferably in an amount of from about 0.005 to about 0.2% by weight (metal), calculated on the starting compound (I).

The pH of the hydrogenation solution is adjusted at a value greater than 7 by the addition of a base. A pH in the range of from about 8 to 10, measured with humid pH paper, is preferred. Suitable bases are the conventional inorganic or organic bases, for example alkali metal hydroxides or alcoholates, such as NaOH, KOH, $NaOCH_3$, $KOCH_3$, $NaOC_2H_5$ and others, or nitrogen bases, for example triethylamine, cyclohexylamine, pyridine and others. They are generally used in an amount of from about 0.0001 to 5% by weight, preferably of from about 0.01 to 2% by weight, in particular of from about 0.1 to 1% by weight, calculated on the substance (I).

The hydrogenation takes place under a hydrogen pressure of from about 0.2 to about at least 200 bars. A pressure of from about 1 to 100 bars, in particular of from about 10 to 50 bars, is preferred.

The hydrogenation proceeds according to the gross equation

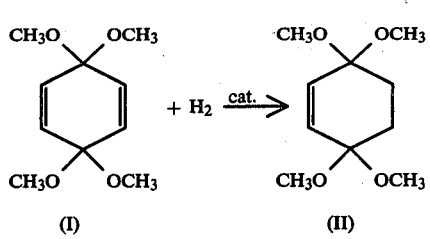

and is performed under said conditions until about 1 mol of hydrogen per mol of compound (I) is consumed. As hydrogenation devices there may be used apparatuses which are conventional for reactions of this type, for example agitator or shaking autoclaves or adequate glass or enamel vessels provided with a stirrer. Upon completion of the hydrogen absorption, the reaction product is treated in known manner, for example by cooling and expanding the reaction vessel, filtering off the catalyst, distilling off the solvent and by subsequently distilling or crystallizing the compound obtained of the formula II.

The highly selective hydrogenation under the indicated reaction conditions yielding cyclohexene diketal is surprising, especially owing to the fact that in subsequent hydrogenation under the same conditions as above, the cyclohexane stage is obtained in smooth manner. The by-products formed depend on the catalyst and on the base employed. Only hydroquinone dimethyl ether and cyclohexane-1,4-dione-tetramethyl diketal are obtained in varying small quantities, these compounds, however, being valuable intermediates.

For the purpose of reketalizing (II) to (II''), the latter diketal having higher alcohol radicals in the ketal groupings, the compound (II) may be isolated in the manner described, be dissolved in an alcohol R'OH which has a primary or secondary alkyl radical R' with 2 to 4 carbon atoms, preferably a primary alkyl radical, and the solution may be acidified with substantial exclusion of water, that is to say that not more than about 0.5% by volume of water should be present. When this alcohol R'OH has already been used as the solvent in the hydrogenation, isolation may be dispensed with. After having filtered off the catalyst, the alcoholic solution may be further employed, for example be acidified at a temperature of from about $-10°$ to $+35°$ C., preferably of from about $0°$ to $+25°$ C., in particular of from about $+5°$ to $+25°$ C., whereby the reketalization yielding the cyclohexene-(1)-dione-(3,6)-tetraalkyl diketal of the formula

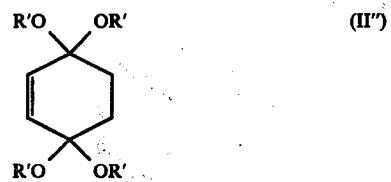

wherein R' is a primary or secondary alkyl radical of from 2 to 4 carbon atoms, takes place. In order to achieve a reaction as complete as possible, the reaction mixture is suitably kept at said temperature range for a certain period of time, preferably of from 2 to at least 5 minutes. It is particularly advantageous to remove the formed methanol by distillation, at said temperature, under reduced pressure.

The alkylketals formed of the formula II'' may be obtained in pure form by further distilling off the alcohol R'OH in a neutral, preferably in a basic medium.

For acidifying upon hydrogenating, there is used a mineral or organic acid, for example $HCl, H_2SO_4, HClO_4$, p-toluenesulfonic acid, formic acid, acetic acid, which should be preferably anhydrous, or acid salts, for example $KHSO_4$, HCl and $H_2SO_4$ being used preferably.

In addition to the quantity of acid which is necessary for neutralizing the bases employed during hydrogenation there is required a quantity of acid in the range of from about 0.0001 to 0.01% by weight, calculated on the batch. For the batch there are used for example about 1 to 50% by weight solutions, preferably about 2 to 10% by weight solutions of (II) in R'OH. The pH of these solutions should be smaller than 7, preferably of from 3 to 4 (measured with humid pH paper).

When acidifying the diketals (II') optionally dissolved in the alcohol ROH and when heating them for a period of time of from about 10 to 60 minutes to a temperature of from about 60° to 120° C., preferably to reflux temperature, they rearrange according to the gross equation

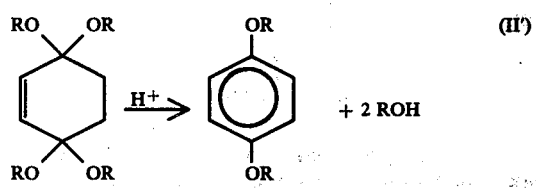

to form the corresponding hydroquinone dialkyl ether, while 2 mols of alcohol are split off; said ethers can be isolated by distillation upon completion of the reaction and upon subsequent neutralization.

Hydroquinone ethers, which are inter alia desired intermediates for the dyestuff preparation, especially for the preparation of yellow pigment dyestuffs, are, consequently, readily accessible by the present invention. A particular advantage of the process according to the present invention resides in the fact that with minimal quantities of salts formed practically no waste waters are obtained and, consequently, the process has little pollution effect.

Since p-benzoquinone-tetramethyl diketal (I) used as the starting material is stable to acids and readily rearranges in trimethoxybenzene in a highly exothermal reaction, an exact checking of the pH is required when operating in an acid medium, whereas a reduction in alkaline medium with subsequent acid-catalyzed splitting off of methanol proceeds more safely and assures a higher yield of hydroquinone dimethyl ether. The cyclohexene-(1)-dione-(3,6)-tetramethyl diketal of the formula (II) obtained on reduction in alkaline medium is a novel compound which is a valuable intermediate to be used in a wide field of application. For example hydroquinone dimethyl ether, which is an intermediate for the preparation of valuable yellow pigment dyestuffs or dyestuff components in photography, may be directly prepared from such diketal according to the invention in known manner. Cyclohexene-(1)-dione-(3,6)-tetramethyl diketal may also be further reduced under the same conditions to cyclohexane-(1,4)-dione-tetramethyl diketal, and by acid hydrolysis of the latter cyclohexane-(1,4)-dione is obtained, which is an important starting product for the field of semiconductors. By reaction with malonitrile to yield 1,4-bis-(dicyanomethylene)-cyclohexane and subsequently with N-bromosuccinimide tetracyanoquinone dimethane, a semiconductor component is obtained (cf. J. Am. Chem. Soc. 84 (1962), 3372).

From the cyclohexene-(1)-dione-(3,6)-tetraalkyl diketals with higher alkyl radicals in the ketal groupings obtainable by reketalization with higher alcohols than methanol from cyclohexene-(1)-dione-(3,6)-tetramethyl diketal (II), there may be prepared in analogous manner the corresponding hydroquinone dialkyl ethers and cyclohexane-(1,4)-dione-tetraalkyl diketals. The cyclohexene-(1)-dione-(3,6)-tetraalkyl diketals, too, are novel compounds.

The following examples illustrate the invention. The solvents used in the examples were technically absolute, that is to say, their water content was less than 0.3% by volume. Insofar as it was operated under pressure, there were used stirrer autoclaves made from stainless steel.

EXAMPLE 1

Cyclohexene-(1)-dione-(3,6)-tetramethyl-ketal 377.6 g (1.886 mol) of p-benzoquinone tetramethyl diketal were dissolved in 1060 g of methanol. Upon addition of 0.5 g of triethylamine and 1 g of Pd supported by animal charcoal (5% concentration) hydrogen was injected at room temperature under a pressure of from 50 to 10 bars. After absorption of 42.5 liters of hydrogen (liters measured under normal conditions of temperature and pressure) over a period of 20 minutes, the pressure was released, the catalyst was filtered off, the solvent (methanol) was distilled off under normal pressure and the reaction product was distilled in vacuo (20 mg Hg) at a temperature of from 110° to 150° C. According to gas chromatographic calibration the distillate consisted of 4% of hydroquinone dimethyl ether, 93% of cyclohexene-(1)-dione-(3,6)-tetramethyl ketal (II) and 2% of tetramethyl ketal of cyclohexanedione-(1,4). The compound (II) distilled substantially at 20° C. and could thus be separated in pure form (melting point: 38° C.).

The yield of II was 343.2 g which corresponded to a yield of 90% of the theory.

EXAMPLE 2

2.103 mols of p-benzoquinone tetramethyl ketal were dissolved in 1005 g of methanol. Upon addition of 5 g of NaOCH$_3$ and 1 g of freshly prepared Raney nickel hydrogen was injected under a pressure of from 80 to 30 bars at room temperature. After absorption of 45 liters of hydrogen over a period of 30 minutes, the pressure was released, the catalyst was filtered off, the solvent was distilled off under normal pressure and the reaction product was subsequently distilled under reduced pressure (20 mm Hg) at a temperature of from 110° to 150° C. According to gas chromatographic analysis the distillate consisted of 11% of hydroquinone dimethyl ether, 80% of cyclohexene-(1)-dione-(3,6)-tetramethyl ketal (II) and of 5% of tetramethyl ketal of cyclohexanedione-(1,4).

EXAMPLE 3

200 g of p-benzoquinone tetramethyl ketal were dissolved in 500 g of methanol, 5 g of NaOCH$_3$ and 1 g of Pt/C (5% concentration) were added and the batch was hydrogenated under a pressure of from 40 to 10 bars until 21 liters of hydrogen were absorbed. Upon pressure release, filtering off of the catalyst and evaporation of the solvent, 203 g of residue were retained, which were distilled. After a first run of 25 g, 173 g of cyclohexene-(1)-dione-(3,6)-tetramethyl ketal having a melting point of 38° C. distilled over at a temperature of from 122° to 130° C. under a pressure of 20 mm Hg. The yield, consequently, was 85% of the theoretical yield.

EXAMPLE 4

85 g of p-benzoquinone tetramethyl ketal were dissolved in 180 g of methanol and 1 g of triethylamine and 1 g of Pt/C (5% concentration) were added. Hydrogen was injected under 30 bars until 8.4 liters were consumed. During this process the temperature rose to 38° C. Upon working up according to Example 1, 75 g of cyclohexene-(1)-dione-(3,6)-tetramethyl ketal could be isolated which corresponded to a yield of 87% of the theory.

EXAMPLE 5

Hydroquinone dimethyl ether 100 g of cyclohexene-(1)-dione-(3,6)-tetramethyl ketal were acidified at room temperature with 0.01 mol of gaseous HCl. Thereafter the formed methanol was evaporated until a bottom temperature of 90° C. was attained, thereafter the mixture was neutralized with NaOCH$_3$ and hydroquinone dimethyl ether was obtained by distillation under 60 bars/130° C. which corresponded to a 90% yield.

EXAMPLE 6

Hydroquinone dimethyl ether

To 100 g of cyclohexene-(1)-dione-(3,6)-tetramethyl ketal was added at room temperature 0.1 g of p-toluenesulfonic acid and the batch was heated to 90° C. until no more methanol distilled over. Subsequently the reaction mixture was neutralized with NaOCH$_3$ and 72.1 g of hydroquinone dimethyl ether distilled in vacuo at 60 bars/130° C.

EXAMPLE 7

Hydroquinone diethyl ether 100 g of cyclohexene-(1)-dione-(3,6)-tetramethyl ketal were dissolved in 1500 g of ethanol at 20° C. and the batch was acidified while stirring with 0.003 g of p-toluenesulfonic acid. After about 10 minutes the batch was refluxed for 30 minutes, neutralized with NaOCH$_3$ and the formed methanol and the solvent were substantially evaporated. The crude yield was 65 g. By recrystallization from ethanol were obtained 57 g of pure hydroquinone diethyl ether having a melting point of 72° C. which corresponded to a yield of 70% of the theory.

EXAMPLE 8

Hydroquinone-di-n-butyl ether 100 g of cyclohexene-(1)-dione-(3,6)-tetramethyl ketal were dissolved in 1500 g of n-butanol at 20° C. and the batch was acidified while stirring with 0.005 g of p-toluenesulfonic acid. After about 10 minutes the batch was heated for 30 minutes to 90° C., subsequently neutralized with NaOCH$_3$, the formed methanol and the solvent were completely evaporated under slightly reduced pressure and subsequently the reaction product was submitted to a fractionating distillation. 65.3 g of hydroquinone dibutyl ether having a melting point of 46° C. distilled over under a pressure of 5 mm Hg at a temperature of from 125° to 135° C., which corresponded to a yield of 60% of the theory.

EXAMPLE 9

Hydroquinone-di-n-butyl ether 50 g of p-benzoquinone tetramethyl ketal were dissolved in 200 g of n-butanol and 1 g of triethylamine and 0.5 g of Pd/C (5% concentration) were added. At room temperature under a pressure of from 50 to 30 bars hydrogen was thereafter injected until 5.5 liters were consumed, whereby the temperature rose to 32° C. The pH of the solution was adjusted at 3 with HCl (at 10° C.), the solution was stirred for 30 minutes and was subsequently heated to 70° C. for 5 minutes. Thereafter butanol and formed methanol were withdrawn on the rotation evaporator and 31 g of hydroquinone dibutyl ether distilled over under 5 mm Hg at a boiling temperature of from 130° to 135° C. The yield, consequently, was 64% of the theory.

EXAMPLE 10

Cyclohexene-(1)-dione-(3,6)-tetra-n-butyl diketal 20 g of cyclohexene-(1)-dione-(3,6)-tetramethyl ketal were dissolved in 250 ml of n-butanol at 0° C., the solution was acidified with 0.03 g of propionic acid and was stirred for 5 minutes, simultaneously formed methanol being withdrawn in vacuo under a pressure of 8 mm Hg. Thereafter the pH of the reaction product was adjusted at an alkaline value of 10 with sodium methylate and excess butanol was distilled off. 29 g of residue were obtained which consisted of 5% of hydroquinone-di-n-butyl ether and 80% of cyclohexene-(1)-dione-(3,6)-tetra-n-butyl diketal according to gas chromatographic analysis.

NMR: (cyclohexene-(1)-dione-(3,6)-tetra-n-butyl diketal):

τ=4.8 (s), 4 H; τ=3.75–4.0, 8 H, triplet τ=0.8 to 1.85, 28 H, multiplet

What is claimed is:

1. Cyclohexene-(1)-dione-(3,6)-tetraalkyl diketals of the formula

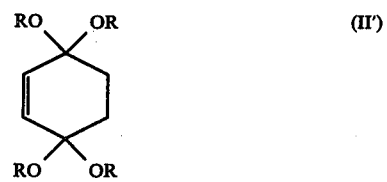

wherein each R represents a primary or secondary C$_{1-4}$ alkyl radical.

2. Cyclohexene-(1)-dione-(3,6)-tetramethyl diketal.

3. A process for the preparation of a cyclohexene-(1)-dione-(3,6)-tetraalkyl diketal as claimed in claim 1, which comprises reducing p-benzoquinone tetramethyl diketal of the formula

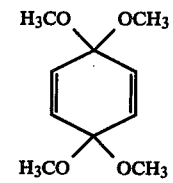

with about 1 mol of hydrogen per mol of diketal in the presence of a hydrogenation catalyst, in a basic medium, at a temperature of from about +10° to +50° C., and optionally reketalizing the cyclohexene-(1)-dione-(3,6)-tetramethyl diketal by treating it with an alcohol having a primary or secondary alkyl moiety of from 2 to 4 carbon atoms, at a temperature of from about −10° to +35° C. in a slightly acidic medium, with substantial exclusion of water.

4. A process as claimed in claim 3, which comprises carrying out the reduction in an alcohol which corresponds to that employed for reketalization.

5. A process as claimed in claim 3, wherein the reduction is carried out at a temperature of from +15° to +40° C.

6. A process as claimed in claim 3, wherein the reketalization is carried out at a temperature of from about 0° to +25° C.

7. A process as claimed in claim 6, wherein the reketalization is carried out at a temperature of from about +5° to +25° C.

8. A process as claimed in claim 3, which comprises carrying out the reduction in the presence of a solvent conventional for use for catalytical hydrogenations.

9. A process as claimed in claim 8 wherein the solvent is methanol.

* * * * *